(12) United States Patent
Zou et al.

(10) Patent No.: US 12,426,950 B2
(45) Date of Patent: Sep. 30, 2025

(54) LASER RESECTOSCOPE FOR MINOR CALIBER

(71) Applicant: THE FIRST AFFILIATED HOSPITAL OF ANHUI MEDICAL UNIVERSITY, Hefei (CN)

(72) Inventors: Zhihui Zou, Hefei (CN); Song Fan, Hefei (CN); Li Zhang, Hefei (CN); Aiping Wang, Hefei (CN); Meng Zhang, Hefei (CN); Shuiping Yin, Hefei (CN); Changsheng Zhan, Hefei (CN); Yongtao Hu, Hefei (CN); Zongyao Hao, Hefei (CN); Chaozhao Liang, Hefei (CN)

(73) Assignees: THE FIRST AFFILIATED HOSPITAL OF ANHUI MEDICAL UNIVERSITY, Hefei (CN); Zhihui Zou, Hefei (CN)

(*) Notice: Subject to any disclaimer, the term of this patent is extended or adjusted under 35 U.S.C. 154(b) by 386 days.

(21) Appl. No.: 18/026,134

(22) PCT Filed: Aug. 20, 2021

(86) PCT No.: PCT/CN2021/113747
§ 371 (c)(1),
(2) Date: Mar. 14, 2023

(87) PCT Pub. No.: WO2022/062791
PCT Pub. Date: Mar. 31, 2022

(65) Prior Publication Data
US 2023/0355307 A1    Nov. 9, 2023

(30) Foreign Application Priority Data
Sep. 23, 2020 (CN) .......................... 202011006647.7

(51) Int. Cl.
*A61B 18/24* (2006.01)
*A61B 18/00* (2006.01)
*A61B 18/22* (2006.01)

(52) U.S. Cl.
CPC .... *A61B 18/24* (2013.01); *A61B 2018/00601* (2013.01); *A61B 2018/2205* (2013.01); *A61B 2218/002* (2013.01)

(58) Field of Classification Search
CPC .......... A61B 18/24; A61B 2018/00601; A61B 2018/2205; A61B 2018/1407;
(Continued)

(56) References Cited

U.S. PATENT DOCUMENTS

| 5,807,240 A | * | 9/1998 | Muller | A61B 1/00135 600/105 |
| 7,503,893 B2 | * | 3/2009 | Kucklick | A61B 1/00135 600/105 |
| 11,666,354 B2 | * | 6/2023 | Shener-Irmakoglu | A61B 1/00068 600/105 |

FOREIGN PATENT DOCUMENTS

| CN | 201505177 U | 6/2010 |
| CN | 201939434 U | 8/2011 |

(Continued)

*Primary Examiner* — Beverly M Flanagan
(74) *Attorney, Agent, or Firm* — Hemisphere Law, PLLC; Zhigang Ma

(57) ABSTRACT

A laser resectoscope for minor caliber includes a water back system, a water inlet system, a laser sheath system, an observation system. The water back system includes a water return pipe and a water outlet structure. The water inlet system includes a water inlet pipe and a water inlet structure. The laser sheath system includes a laser sheath, an optical fiber and a laser head. The observation system includes a mirror tube and an eyepiece. It is increased for the water return of the laser resectoscope, and the laser resectoscope (Continued)

in F24 can be used to meet the surgical requirements of the conventional laser resectoscope in F26 clinically.

9 Claims, 6 Drawing Sheets

(58) Field of Classification Search
CPC .... A61B 2018/00505; A61B 2218/001; A61B 2218/002
USPC ............................................ 606/41; 600/105
See application file for complete search history.

(56) References Cited

FOREIGN PATENT DOCUMENTS

| | | | |
|---|---|---|---|
| CN | 203873732 U | 10/2014 | |
| CN | 204394448 U | 6/2015 | |
| CN | 208274811 U | 12/2018 | |
| CN | 209153969 U | 7/2019 | |
| CN | 111544082 A | 8/2020 | |
| WO | WO-0047116 A1 * | 8/2000 | ............. A61B 1/015 |
| WO | WO-2005104966 A1 * | 11/2005 | ............. A61B 17/29 |
| WO | WO-2016185102 A1 * | 11/2016 | ........... A61B 18/149 |

* cited by examiner

LASER RESECTOSCOPE FOR MINOR CALIBER

FIELD OF THE INVENTION

The present invention relates to laser resectoscopes in the field of medical technology, and more particularly to a laser resectoscope for minor caliber.

BACKGROUND OF THE INVENTION

Transurethral electrotomy is one of the most common techniques in urology, which can treat diseases such as prostatic hyperplasia or bladder tumor safely and effectively. It refers to the insertion of transurethral resection scope, under direct vision to remove prostate hyperplasia or urinary tract tumors and other tissues. Typically, the surgeon excises the abnormal tissue with an electrocutting mirror. The electrocutting mirror has a long rod and allows viewing of the surgical area with an optical system and associated lighting. The electrocutting mirror also has a slider that can be moved longitudinally by the hand and can drive the resecting instrument to move, for example, subjected to high-frequency ring electrodes or laser fibers radiated at the distal end. If the electrocutting mirror is used in urology for removing prostate tissue or urinary tumors, the laser resectoscope for minor caliber can also be used to cut, vaporize or enucleate the tissue by laser or combined with the lens sheath.

During use, the traditional laser resectoscope with 26 F (F is the unit of circumferential diameter) can meet the needs of most people. But, there are still some patients whose urethral size is too small to complete the operation with the electrocutting mirror of this size. If the circumferential diameter is changed F24 to F26, the water back system of the laser resectoscope is reduced accordingly, and it is severely reduced for diverting bleeding. As a result, the surgical field of vision is blurred with bleeding and cannot be sustained.

SUMMARY OF THE INVENTION

In order to solve the problems that the waste cannot be discharged in time as the traditional laser resectoscope being minification, the present invention provides a laser resectoscope for minor caliber.

The present invention adopts the following technical scheme: a laser resectoscope for minor caliber, includes:
  a water back system, including a water return pipe and a water outlet structure; one end of the water return pipe connected with the water outlet structure, a plurality of water return holes defined on the surrounding of the other end of the water return pipe; the water outlet structure used to discharge reclaimed water from the plurality of water return holes to the water return pipe;
  a water inlet system, including a water inlet pipe and a water inlet structure; the water inlet pipe inserted in the water return pipe; one end of the water inlet pipe connected with the water inlet structure, and the other end of the water inlet pipe able to extend outside the water return pipe; the water inlet pipe being curve triangular in cross section, and the cross section area of the water inlet pipe being less than a half of the cross section area of the water outlet pipe; the water inlet structure used to provide cooling water to the water inlet pipe;
  a laser sheath system, including a laser sheath, an optical fiber and a laser head; the laser sheath inserted in the water inlet pipe, and able to extend outside the water inlet pipe, the optical fiber inserted in the laser sheath; the laser head connected to the optical fiber, and able to extend out of the laser sheath;
  an observation system, including a mirror tube and an eyepiece; the mirror tube inserted into one end of the water inlet pipe, able to extend to the other end of the water inlet pipe; the center of the mirror tube being on the side near the water return pipe; a diagonal plane defined on the end of the mirror tube near the water inlet pipe, and the diagonal plane being towards to the end of the laser sheath; the eyepiece used to view an image at the water inlet pipe through the mirror tube.

In the laser resectoscope of the present invention, the surgical site is determined by the mirror tube and the eyepiece together, the vitrectomy of the surgical site is operated by the optical fiber laser and the laser head together, the cooling water which cleans and cools the organization generated by the vitrectomy is supplied by the water inlet pipe. Because of the vitrectomy the waste liquid is collected and discharged by the water back system. As the cross section of the water inlet pipe being curve triangular, and the cross section area of the water inlet pipe being less than a half of the cross section area of the water outlet pipe, it is increased for the reclaimed water. Especially in small laser cutting, enough sewage can be discharged immediately and the definition of the eyepiece can be increased. It solves the problem that sewage cannot be discharged immediately because of the size shrinking of the laser resectoscope, and it is improved for the definition with positive effect.

In the laser resectoscope of the present invention, the laser sheath system further includes a fixed loop; the fixed loop is arranged between the laser sheath and the mirror tube, and is used to connect the laser sheath to the mirror tube.

In the laser resectoscope of the present invention, the laser sheath, the water inlet pipe, and the mirror tube are arranged in parallel axial direction, and the length of the laser sheath exposed outside the water inlet pipe is greater than the length of the mirror tube exposed outside the water inlet pipe.

In the laser resectoscope of the present invention, the water circumference of the return pipe is 24 F.

In the laser resectoscope of the present invention, the difference between the length of the laser sheath exposed outside the water inlet pipe and the length of the mirror tube exposed outside the water inlet pipe is 2-3 mm, the diameter of the laser head is 0.8 mm, and the diameter of the laser sheath is 1.2 mm.

In the laser resectoscope of the present invention, further includes a hand-held system; the hand-held system includes a handle and an inserted-connected structure; the inserted-connected structure is inserted into the water inlet structure, and the handle is fixed on the inserted-connected structure; both the laser sheath and the mirror tube after passing through the inserted-connected structure and the water inlet structure, are placed together in the water inlet pipe.

In the laser resectoscope of the present invention, the plurality of water return holes are divided into multiple groups which includes a plurality of the first groups and a plurality of the second groups; the water return holes in the first groups have larger aperture than the water return holes in the second groups'; every the first group is between the two adjacent second groups, and the total of the water return holes in every first group is more than the he total of the water return holes in every second group.

In the laser resectoscope of the present invention, further includes:

a mounting seat, the laser sheath inserted in the mounting seat, the mirror tube being through the mounting seat; the eyepiece connected with the lens tube;

an adjusting system, including a pull ring, a first pull rod and a second pull rod; one end of the second pull rod installed rotatedly on the side wall of the eyepiece, and the other end of the second pull rod connected rotatedly with one end of the first pull rod; the middle of the first pull rod rotated and installed on the side wall of the mounting seat, and the other end of the first pull rod connected fixedly with the pull ring.

In the laser resectoscope of the present invention, the water inlet structure includes a first step sleeve ring, a first tangential pipe and a water inlet valve; the first step sleeve ring is connected with the water inlet pipe, and a water inlet hole communicated with the water inlet pipe is defined in the sidewall of the first step sleeve; the first tangential pipe is inserted into the water inlet hole, and is fixed with the first step sleeve ring; the water inlet valve is installed on the first tangential pipe, and is used to adjust the flow of the first tangential pipe;

the water outlet structure includes a second step sleeve ring, a second tangential pipe and a water outlet valve; one end of the second step sleeve ring is connected with the water return pipe, and the other end of the second step sleeve ring is connected with the first step sleeve ring; a water outlet hole communicated with the water return pipe is defined in the side wall of the second step sleeve ring, and the second tangential pipe is inserted in the water outlet hole and is fixed with the second step sleeve ring.

In comparison with the traditional laser resectoscope for minor caliber, the laser resectoscope of the present invention has the following beneficial effects.

1. In the laser resectoscope of the present invention, the surgical site determined by the mirror tube and the eyepiece together, the vitrectomy of the surgical site is operated by the optical fiber laser and the laser head together, the cooling water which cleans and cools the organization generated by the vitrectomy is supplied by the water inlet pipe. Because of the vitrectomy the waste liquid is collected and discharged by the water back system. As the cross section of the water inlet pipe being curve triangular, and the cross section area of the water inlet pipe being less than a half of the cross section area of the water outlet pipe, it is increased for the reclaimed water. Especially in small laser cutting, enough sewage can be discharged immediately and the definition of the eyepiece can be increased. It solves the problem that sewage cannot be discharged immediately because of the size shrinking of the laser resectoscope, and it is improved for the definition with positive effect.

2. As the exposed length of the laser sheath larger than that of the mirror tube, and the oblique section which can increase the field of vision at the end of the laser sheath, then the vision of the eyepiece on the cutting area is expanded, and it is convenient for doctors to perform cutting operations to improve the surgical efficiency. In addition, the length difference of 2-3 mm can maximize the surgical area in the eyepiece, avoiding the narrow surgical field caused by water impact or tissue occlusion, then it is improved for the effect of the equipment.

3. in comparison with the traditional laser resectoscope of 26F, 24 F of the laser resectoscope of the present invention can meet the needs of more patients. First of all, it can reduce the incidence of urethral stricture after transurethral surgery, and solve the problem that some patients with thin urethra cannot enter the scope due to the use of standard F26 laser electrocutting mirror. At the same time, it can ensure the full use of the water for cleaning and cooling, effectively reduce the high temperature of the laser head, prevent the burning of the laser head, on the other hand, it does not affect the effect of flushing and reflux in the laser transurethral surgery, which is convenient for laser surgery.

4. As the plurality of water return holes being divided into multiple groups which includes a plurality of the first groups and a plurality of the second groups, the two kinds of groups being arranged alternately, the small aperture of the water return holes being dense, and the large aperture of the water return holes being relatively sparse, it is improved for the efficiency of the sewage and the decrement rate of the blockage.

5. The beneficial effect of the cutting method of the laser resectoscope would not be described here because that it is the same of the laser resectoscope's.

BRIEF DESCRIPTION OF THE DRAWINGS

The above objects and advantages of the present invention will become more readily apparent to those ordinarily skilled in the art after reviewing the following detailed description and accompanying drawings, in which.

Appended drawing references are shown as follow:

| | |
|---|---|
| 1 | water return pipe |
| 2 | water return holes |
| 3 | water inlet pipe |
| 4 | laser sheath |
| 5 | laser head |
| 6 | mirror tube |
| 7 | eyepiece |
| 8 | fixed loop |
| 9 | handle |
| 10 | inserted-connected structure |
| 11 | mounting seat |
| 12 | pull ring |
| 13 | first pull rod |
| 14 | second pull rod |
| 15 | first step sleeve ring |
| 16 | first tangential pipe |
| 17 | water inlet valve |
| 18 | second step sleeve ring |
| 19 | second tangential pipe |
| 20 | water outlet valve |
| 21 | first group |
| 22 | second group |
| 23 | first hole |
| 24 | second hole |

DETAILED DESCRIPTION OF PREFERRED EMBODIMENTS

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

First Embodiment

Figure 1:
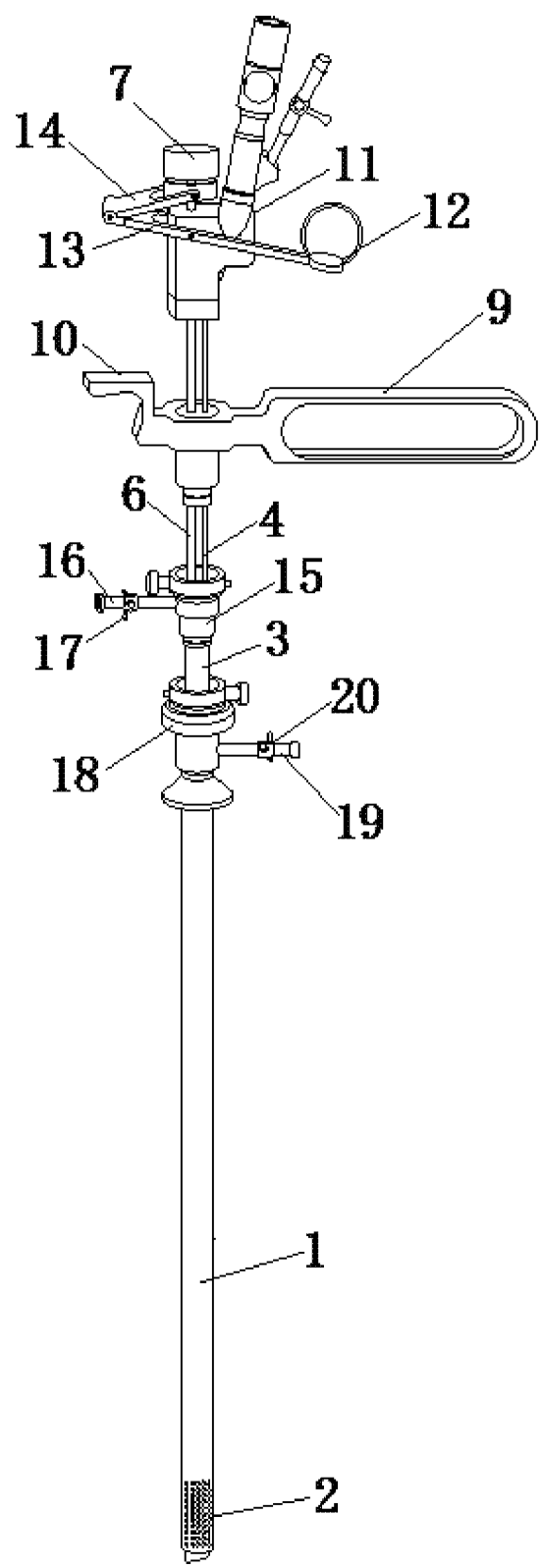
FIG. 1 is a schematic diagram of a stereochemical structure of a laser resectoscope for minor caliber, according to an example embodiment.
Figure 2:
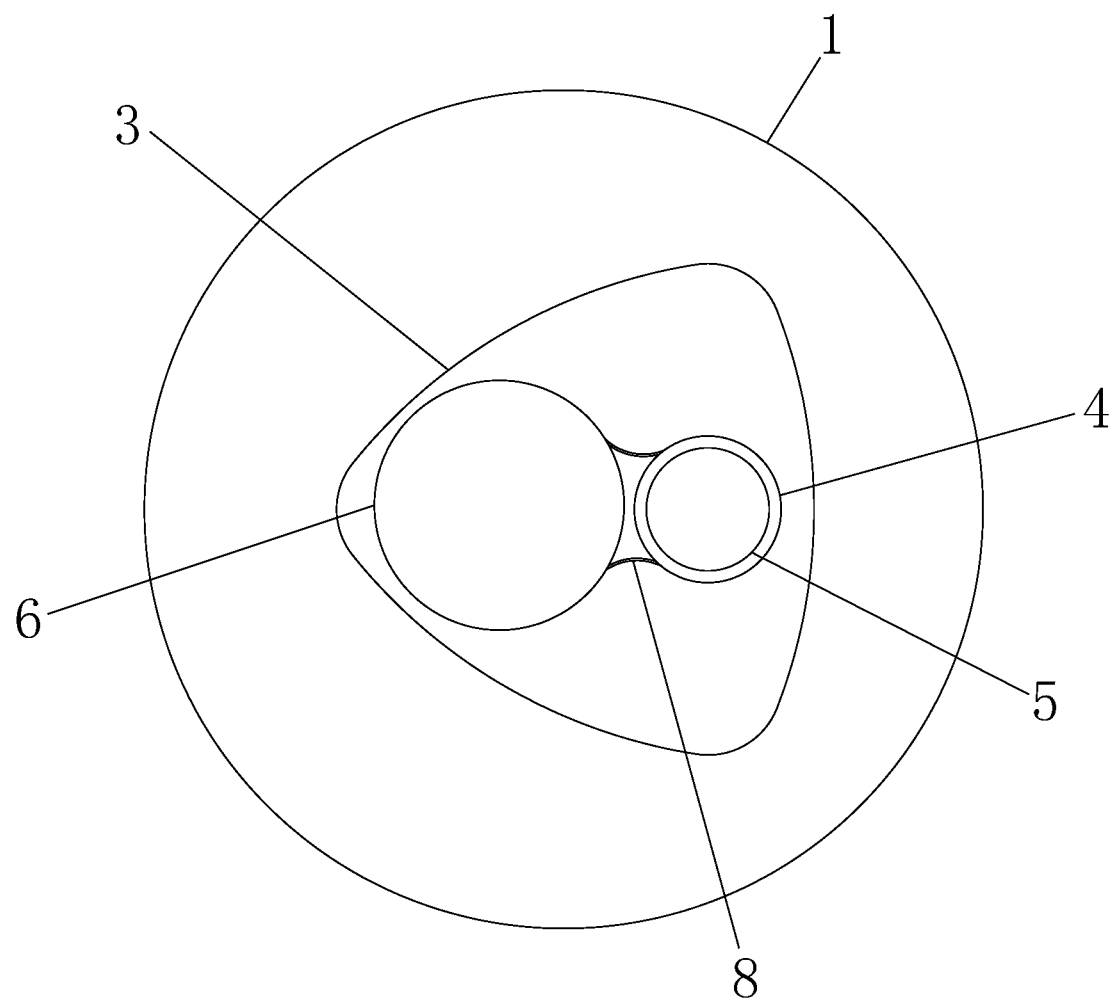
FIG. 2 is a schematic diagram with a vertical view of the laser resectoscope of FIG. 1.
Figure 3:
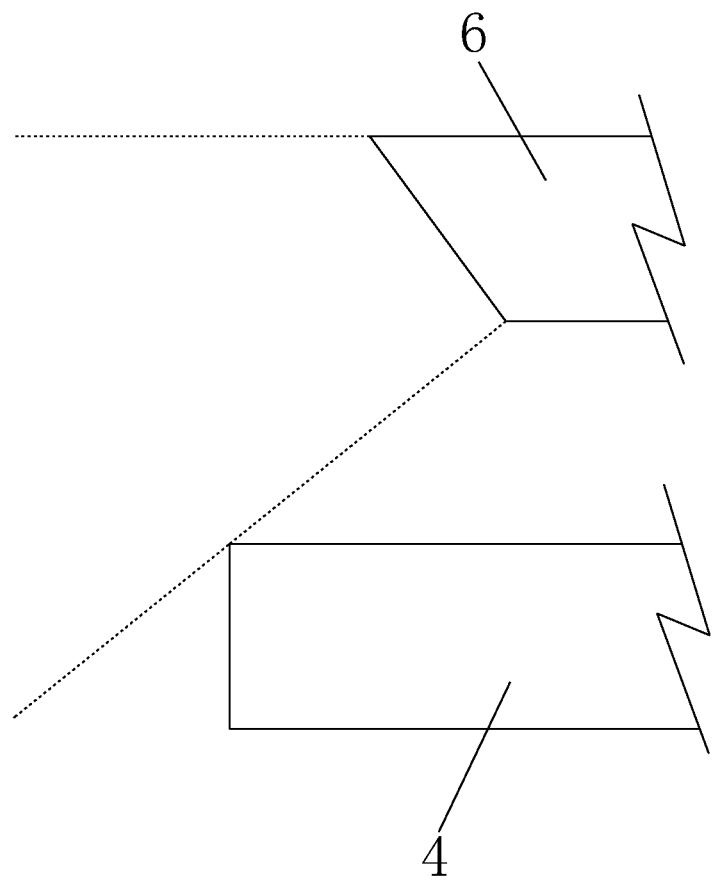
FIG. 3 is a comparison diagram of the difference between a laser sheath and a mirror tube of the laser resectoscope of FIG. 1.

Referring to FIGS. 1, 2 and 3, a laser resectoscope for minor caliber is shown as an embodiment. The laser resectoscope can be used for excision of hyperplasia of prostate, other prostate medical operations, and all transurethral diseases such as bladder and tumor. In present embodiment, the laser resectoscope includes a water back system, a water inlet system, a laser sheath system, an observation system, a hand-held system, a mounting seat 11 and an adjusting system.

The water back system includes a water return pipe 1 and a water outlet structure. One end of the water return pipe 1 is connected with the water outlet structure, and a plurality of water return holes 2 is defined on the surrounding of the other end of the water return pipe 1. The circumference of the water return pipe 1 is 24 F to accommodate to the Asian people. In comparison with the traditional laser resectoscope of 26 F, the length of the water return pipe 1 is increased to accommodate to patients with thin urethra, and the injury can be avoid. The water outlet structure is used to discharge reclaimed water from the water return pipe 1 which is collected by the plurality of water return holes 2. In the present embodiment, the water outlet structure includes a second step sleeve ring 18, a second tangential pipe 19 and a water outlet valve 20. One end of the second step sleeve ring 18 is connected with the water return pipe 1, and a water outlet hole communicated with the water pipe 1 is defined in the sidewall of the second step sleeve ring 18. One end of the second tangential pipe 19 is inserted into the outlet hole and is fixed to the second step sleeve ring 18. During the operation, the water return pipe 1 will be located at the surgical site, and the tissue generated in the process of laser cutting will be mixed with the water for cleaning and cooling to form waste liquid. The waste liquid will be recycled as recovery water through the external equipment, so that there will not be too much water in the surgical area and the tissue can be effectively removed. As for the pump power required in the water back process, it depends on the amount of waste liquid generated during the actual operation. The recovery power is related to the amount of waste liquid generated per unit time and the diameter of the recovery pipe. The waste liquid recovered by the system can be treated with specialized medical equipment to prevent contamination of the waste liquid. Of course, in the other embodiments, the recovery system can also include pumps, a waste liquid treatment equipment, etc., so that the laser resectoscope can be used easily.

The water inlet system includes a water inlet pipe 3 and a water inlet structure. The water inlet pipe 3 is inserted in the water return pipe 1 and is in the central of the water return pipe 1. One end of the water inlet pipe 3 is connected with the water inlet structure, and the other end of the water inlet pipe 3 is able to extend outside the water inlet pipe 3. The water inlet pipe 3 is curve triangular in cross section, and the cross section area of the water inlet pipe 3 is less than a half of the cross section area of the water outlet pipe 1. Then it is increased greatly for water to back. Especially, when the size of the laser resectoscope is small, the sewage can be discharged immediately because of enough water. The water inlet structure is used to supply water to the water inlet pipe 3 for cleaning and cooling. In the present embodiment, the water inlet structure includes a first step sleeve ring 15, a first tangential pipe 16 and a water inlet valve 17. The first step sleeve ring 15 is connected with the water inlet pipe 3, and a water inlet hole communicated with the water inlet pipe 3 is defined in the sidewall of the first step sleeve 15. The first tangential pipe 16 is inserted into the water inlet hole, and is fixed with the first step sleeve ring 15. The water inlet valve 17 is installed on the first tangential pipe 16, and is used to adjust the flow of the first tangential pipe 16. The water inlet structure can be used for external equipment to input the water for cleaning and cooling. The water reaches the first step sleeve ring 15 after passing the first through tangential pipe 16, and further enters into the water inlet pipe 3 ultimately. The water inlet pipe 3 would spray the water, so as to clean and cool the operation area and facilitate the operation. The inflow of the adjusting system can be adjusted by the doctor with the water inlet valve 17, and the outflow of the back water system can be adjusted with the water outlet valve 20. Then it can achieve dynamic balance for the water inlet and the water outlet in the operation area, and can be convenient for the operation. A reference scale can be set according to the difference between the water inlet valve 17 and water outlet valve 20, the it can be maintained between the water inlet and the water outlet.

The laser sheath system includes a laser sheath 4, an optical fiber, a laser head 5, and a fixed loop 8. The laser sheath 4 is inserted in the water inlet pipe 3, and is able to extend outside the water inlet pipe 3. The central of the laser sheath 4 is located on the side of water inlet pipe 3 near the water return pipe 1. The laser sheath 4 is a round tube, which has the same shape as the water return pipe 1. The laser sheath 4 is not in the center of the water return pipe 1. The optical fiber is inserted into the laser sheath 4. The optical fiber can be a laser fiber, which can conduct high-power laser.

The laser head 5 is connected with the optical fiber, and can be able to extend out of the laser sheath 4 to cut the surgical tissue controlled under the laser sheath 4. The fixed loop 8 is arranged between the laser sheath 4 and the mirror tube 6, and is used to connect the laser sheath 4 to the mirror tube 6. In the present invention, the diameter of the laser head 5 is 0.8 mm, and the diameter of the laser sheath 4 is 1.2 mm, the it is easy for cutting nicely. Of course, in other embodiments, the dimensions of the laser head 5 and the laser sheath 4 can be the same, and it would be best if the dimensions are depended on the surgical requirements. For example, when the cutting accuracy is demanded relatively high, the size should be reduced to reduce the error, on the contrary, the size can be increased to improve the stability.

The observation system includes a mirror tube 6 and an eyepiece 7. In other embodiments, the observation system also can include an objective used for observing the other areas, further can include a refractor used for bending the light. The mirror tube 6 is inserted into the water inlet pipe 3, and is able to extend outside the water inlet pipe 3. The center of the mirror tube 6 is on the side near the water return pipe 1. The eyepiece 7 is used to view an image at the water inlet pipe 3 through the mirror tube 6. In the present invention, the laser sheath 3, the water inlet pipe 3, and the mirror tube 6 are arranged in parallel axial direction. The length of the laser sheath 3 exposed outside the water inlet pipe 3 is greater than the length of the mirror tube 6 exposed outside the water inlet pipe 3. A diagonal plane is defined on the end of the mirror tube 6 near the water inlet pipe 3, and the diagonal plane is towards to the end of the laser sheath 4. Then it is increased for the view of the laser sheath 4, it is also enlarged for the view of the eyepiece 7, and it is convenient for doctors to perform cutting surgery and improve the surgical efficiency. Then it is increased for the view of the laser sheath 4, it is also enlarged for the view of the eyepiece 7, and it is convenient for doctors to perform cutting surgery and improve the surgical efficiency.

The hand-held system includes a handle 9 and an inserted-connected structure 10. The inserted-connected structure 10 is inserted into the water inlet structure, and the handle 9 is fixed on the inserted-connected structure 10. Both the laser sheath 4 and the mirror tube 6 after passing through the inserted-connected structure 10 and the water inlet structure, are placed together in the water inlet pipe 3. The handle 9 is used for the doctor to hold the laser resectoscope, then it is easy to insert the electrocutting mirror into the patient's prostate. The inserted-connected structure 10 is used as a localization structure for the handle 9, the laser sheath 4, and the mirror tube 6. Then it is convenient for doctors to insert laser sheath 4 and mirror tube 6 into the back water system. In addition, the inserted-connected structure 10 can form a seal with the water inlet structure to prevent water flowing out.

The laser sheath 4 is inserted in the mounting seat 11, the other end of the mirror tube 6 is through the mounting seat 11. The eyepiece 7 is connected with the mirror tube 6. The other instruct also can be set on the mounting seat 11 for facilitating the optical fibers to pass through the mounting seat 11. The mounting seat 11 is connected to the inserted-connected structure 10 to form an integrative structure. Then it is easily for doctors to operate, especially to adjust the position of the eyepiece 7.

The adjusting system includes a pull ring 12, a first pull rod 13, and a second pull rod 14. One end of the second pull rod 14 is installed rotatedly on the side wall of the eyepiece 7, and the other end of the second pull rod 14 is connected rotatedly with one end of the first pull rod 13. The middle of the first pull rod 13 is rotated and installed on the side wall of the mounting seat 11, and the other end of the first pull rod 13 is connected fixedly with the pull ring 12. When it is necessary to adjust the relative position of the eyepiece 7 or the position of the mirror tube 6 at the surgical site, the doctor can operate ring-pull 12 to drive the first pull rod 13 to rotate and to drive the second pull rod 14 accordingly. Then the relative position of eyepiece 7 and the mirror tube 6 is changed.

In conclusion, in comparison with the traditional laser resectoscope for minor caliber, the laser resectoscope of the present invention has the following beneficial effects:

(1) In the laser resectoscope of the present invention, the surgical site determined by the mirror tube and the eyepiece together, the vitrectomy of the surgical site is operated by the optical fiber laser and the laser head together, the cooling water which cleans and cools the organization generated by the vitrectomy is supplied by the water inlet pipe. Because of the vitrectomy the waste liquid is collected and discharged by the water back system. As the cross section of the water inlet pipe being curve triangular, and the cross section area of the water inlet pipe being less than a half of the cross section area of the water outlet pipe, it is increased for the reclaimed water. Especially in small laser cutting, enough sewage can be discharged immediately and the definition of the eyepiece can be increased. It solves the problem that sewage cannot be discharged immediately because of the size shrinking of the laser resectoscope, and it is improved for the definition with positive effect.

(2) As the exposed length of the laser sheath larger than that of the mirror tube, and the oblique section which can increase the field of vision at the end of the laser sheath, then the vision of the eyepiece on the cutting area is expanded, and it is convenient for doctors to perform cutting operations to improve the surgical efficiency. In addition, the length difference of 2-3 mm can maximize the surgical area in the eyepiece, avoiding the narrow surgical field caused by water impact or tissue occlusion, then it is improved for the effect of the equipment.

(3) In comparison with the traditional laser resectoscope of 26F, 24 F of the laser resectoscope of the present invention can meet the needs of more patients. First of all, it can reduce the incidence of urethral stricture after transurethral surgery, and solve the problem that some patients with thin urethra cannot enter the scope due to the use of standard F26 laser electrocutting mirror. At the same time, it can ensure the full use of the water for cleaning and cooling, effectively reduce the high temperature of the laser head, prevent the burning of the laser head, on the other hand, it does not affect the effect of flushing and reflux in the laser transurethral surgery, which is convenient for laser surgery.

Second Embodiment

Figure 4:
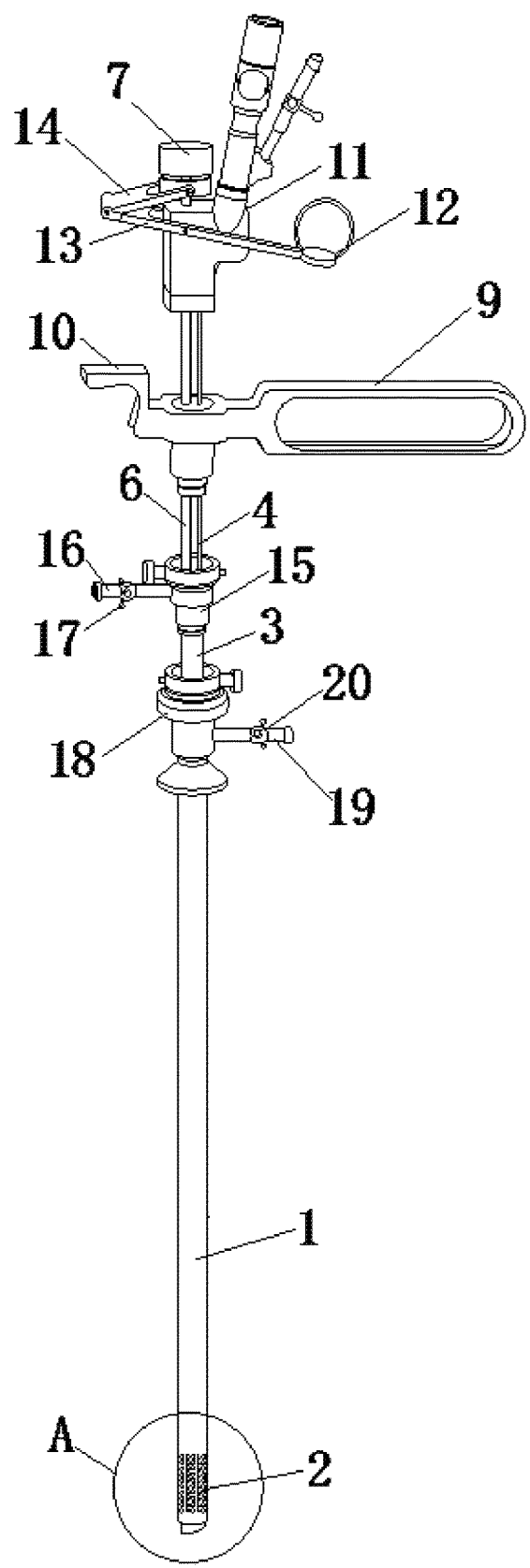
FIG. 4 is a schematic diagram of a stereochemical structure of a laser resectoscope for minor caliber, according to another example embodiment.
Figure 5:
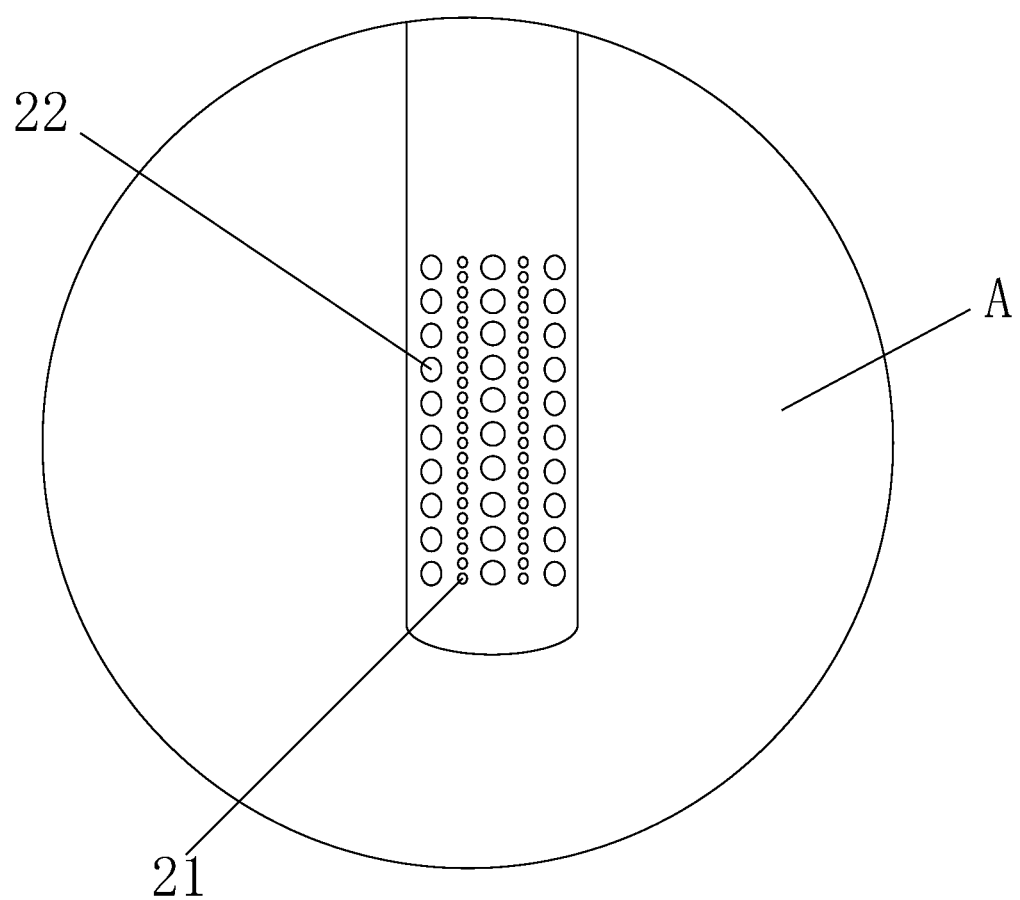
FIG. 5 is a larger version of a district A of the laser resectoscope of FIG. 4.

Referring to FIGS. 4 and 5, another laser resectoscope for minor caliber is shown as a second embodiment. The difference between the first embodiment and the second embodiment is the plurality of water return holes 2. In this embodiment, the plurality of water return holes 2 are divided into two type groups which are defined first groups and second groups. The water return holes 2 in the first groups are defined first water return holes 21, and the water return holes 2 in the second groups are defined second water return holes 22. The first water return holes 21 have larger aperture than the second water return holes 22. Every the first group is between the two adjacent second groups, and the total of the first water return holes 21 in every first group is more than the total of the second water return holes 22 in every second group. Then, it is improved for the water back efficiency and it is reduced for clogging.

Third Embodiment

Figure 6:
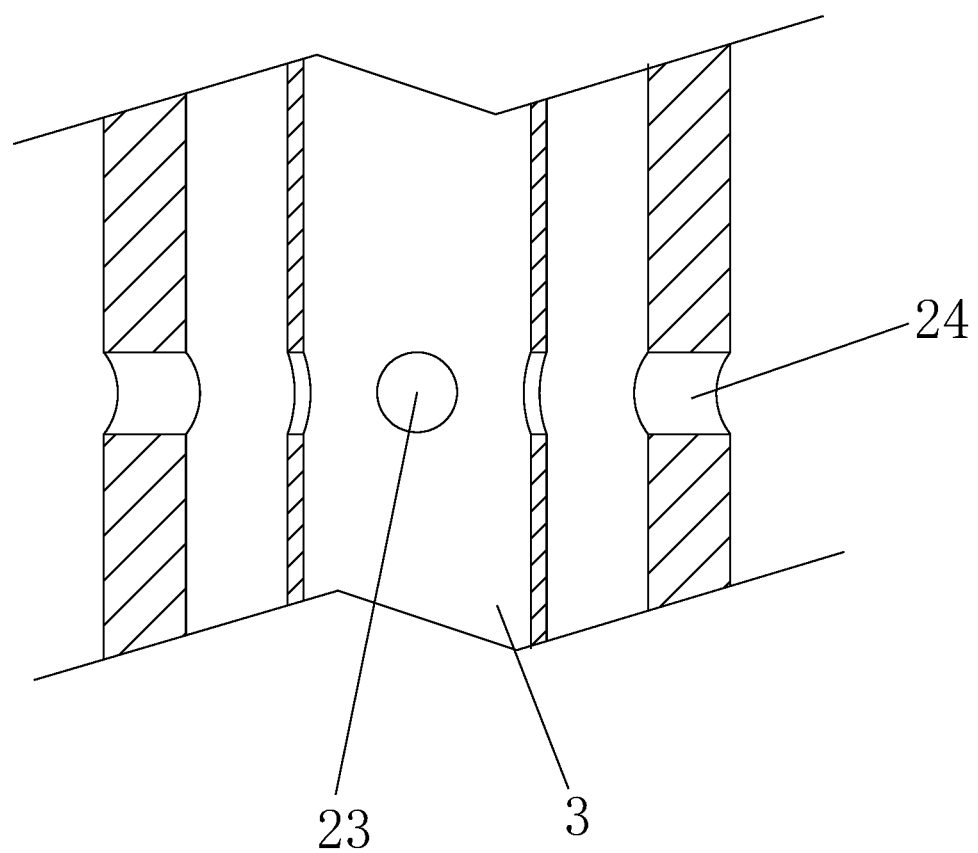
FIG. 6 is a partial schematic diagram of a water inlet system of a laser resectoscope for minor caliber, according to a third example embodiment.

Referring to FIG. 6, a third laser resectoscope for minor caliber is shown as a third embodiment. The difference between the second embodiment and the third embodiment is the channel between the water inlet pipe 3 and the water inlet structure. In this embodiment, a plurality of first holes 23 is arranged in the sidewall of the water inlet structure, and a plurality of second holes 24 is arranged in the sidewall of the water inlet pipe 3. The plurality of first holes 23 and the plurality of second holes 24 are located in the same radial direction. In this way, when entering water, it can disperse the water to flow quickly under the guide of the plurality of first holes 23 and the plurality of second holes 24. In some embodiments, the connection with the water return pipe 1 and the water outlet structure may be set similarly in order to discharge quickly.

Fourth Embodiment

In this embodiment, a cutting method of the laser resectoscopes which both are described in the second embodiment and the third embodiment is provided. The method includes the following steps.

(1) Observe the image at the other end of inlet pipe 3 through eyepiece 7, and use the laser sheath system to perform laser cutting on the surgical site. This step is the observation and laser cutting step, that is, observe whether the electrocutting mirror reaches the site required for the operation, and then send the laser to the laser head 5 through the optical fiber. The laser head 5 gathers the laser and irradiates the tissue of the patient. The tissue is killed and cut by the laser irradiation, and the pathological or proliferative tissue is removed.

(2) Spray water for cleaning and cooling to the cutting part through the water inlet system, and discharge the waste liquid generated by laser cutting through the water back system. This step is realized in the process of cutting, that is, while spraying the water for cleaning and cooling at the cutting place for flushing and cooling, while discharging the waste liquid mixed with the water and the tissue to ensure the smooth operation.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A laser resectoscope for minor caliber, comprising:
    a water back system, comprising a water return pipe and a water outlet structure; one end of the water return pipe connected with the water outlet structure, a plurality of water return holes defined on the surrounding of the other end of the water return pipe; the water outlet structure used to discharge reclaimed water from the plurality of water return holes to the water return pipe;
    a water inlet system, comprising a water inlet pipe and a water inlet structure; the water inlet pipe inserted in the water return pipe; one end of the water inlet pipe connected with the water inlet structure, and the other end of the water inlet pipe able to extend outside the water return pipe; the water inlet pipe being curve triangular in cross section, and the cross section area of the water inlet pipe being less than half of the cross section area of the water outlet pipe; the water inlet structure used to provide cooling water to the water inlet pipe;
    a laser sheath system, comprising a laser sheath, an optical fiber and a laser head; the laser sheath inserted in the water inlet pipe, and able to extend outside the water inlet pipe, the optical fiber inserted in the laser sheath; the laser head connected to the optical fiber, and able to extend out of the laser sheath;
    an observation system, comprising a mirror tube and an eyepiece; the mirror tube inserted into one end of the water inlet pipe, able to extend to the other end of the water inlet pipe; the center of the mirror tube on the side near the water return pipe; a diagonal plane defined on the end of the mirror tube near the water inlet pipe, and the diagonal plane being towards to the end of the laser sheath; the eyepiece used to view an image at the water inlet pipe through the mirror tube;
    a mounting seat; and
    an adjusting system, comprising a pull ring, a first pull rod and a second pull rod; one end of the second pull rod is installed rotatedly on the side wall of the eyepiece, and the other end of the second rod is connected rotatedly with one end of the first pull rod; the middle of the first pull rod rotated and installed on the side wall of the mounting seat, and the other end of the first pull rod connected fixedly with the pull ring, a position of the eyepiece or the mirror tube is adjustable by the adjusting system.

2. The laser resectoscope according to claim 1, wherein the laser sheath system further comprises a fixed loop; the fixed loop is arranged between the laser sheath and the mirror tube, and is used to connect the laser sheath to the mirror tube.

3. The laser resectoscope according to claim 1, wherein the laser sheath, the water inlet pipe, and the mirror tube are arranged in parallel axial direction, and the length of the laser sheath exposed outside the water inlet pipe is greater than the length of the mirror tube exposed outside the water inlet pipe.

4. The laser resectoscope according to claim 3, wherein the water circumference of the water return pipe is 24 F.

5. The laser resectoscope according to claim 4, wherein the difference between the length of the laser sheath exposed outside the water inlet pipe and the length of the mirror tube exposed outside the water inlet pipe is 2-3 mm, the diameter of the laser head is 0.8 mm, and the diameter of the laser sheath is 1.2 mm.

6. The laser resectoscope according to claim 1, further comprising:
    a hand-held system;
    wherein the hand-held system comprises a handle and an inserted-connected structure; the inserted-connected structure is inserted into the water inlet structure, and the handle is fixed on the inserted-connected structure; both the laser sheath and the mirror tube after passing through the inserted-connected structure and the water inlet structure, are placed together in the water inlet pipe.

7. The laser resectoscope according to claim 1, wherein the plurality of water return holes are divided into multiple groups which comprises a plurality of the first groups and a plurality of the second groups; the water return holes in the first groups have larger aperture than the water return holes in the second groups; every the first group is between the two adjacent second groups, and the total of the water return holes in every first group is more than the total of the water return holes in every second group.

8. The laser resectoscope according to claim 6, wherein the laser sheath inserted in the mounting seat, the mirror tube being through the mounting seat; the eyepiece connected with the mirror tube.

9. The laser resectoscope according to claim 8, wherein the water inlet structure comprises a first step sleeve ring, a first tangential pipe and a water inlet valve; the first step sleeve ring is connected with the water inlet pipe, and a water inlet hole communicated with the water inlet pipe is defined in the sidewall of the first step sleeve; the first tangential pipe is inserted into the water inlet hole, and is fixed with the first step sleeve ring; the water inlet valve is installed on the first tangential pipe, and is used to adjust the flow of the first tangential pipe;
    the water outlet structure comprises a second step sleeve ring, a second tangential pipe and a water outlet valve; one end of the second step sleeve ring is connected with the water return pipe, and the other end of the second step sleeve ring is connected with the first step sleeve ring; a water outlet hole communicated with the water return pipe is defined in the side wall of the second step sleeve ring, and the second tangential pipe is inserted in the water outlet hole and is fixed with the second step sleeve ring.

* * * * *